United States Patent [19]
Cohen et al.

[11] Patent Number: 5,886,003
[45] Date of Patent: Mar. 23, 1999

[54] METHODS OF TREATING OR AMELIORATING THE SYMPTOMS OF VENOMOUS BITES AND STINGS

[75] Inventors: Marlene Lois Cohen, Carmel; Kirk Willis Johnson, Camby, both of Ind.

[73] Assignee: Eli Lilly and Company, Indianapolis, Ind.

[21] Appl. No.: 813,131

[22] Filed: Mar. 7, 1997

Related U.S. Application Data

[60] Provisional application No. 60/014,039, Mar. 25, 1996.
[51] Int. Cl.$^6$ .................................................. A61K 31/44
[52] U.S. Cl. ........................... 514/280; 514/285; 514/292
[58] Field of Search ................................... 514/280, 292, 514/285

[56] References Cited

U.S. PATENT DOCUMENTS

| | | | |
|---|---|---|---|
| 4,520,024 | 5/1985 | Cohen | 514/255 |
| 4,563,461 | 1/1986 | Cohen et al. | 514/288 |
| 4,902,691 | 2/1990 | Cohen et al. | 514/288 |
| 4,931,447 | 6/1990 | Foreman et al. | 514/288 |
| 4,981,859 | 1/1991 | Foreman et al. | 514/288 |
| 5,141,944 | 8/1992 | Cohen et al. | 514/288 |
| 5,466,688 | 11/1995 | Commons et al. | 514/212 |

FOREIGN PATENT DOCUMENTS

| | | |
|---|---|---|
| 620222 | 10/1994 | European Pat. Off. . |
| WO 91/02527 | 3/1991 | WIPO . |
| WO 91/14184 | 9/1991 | WIPO . |
| WO 91/16323 | 10/1991 | WIPO . |
| WO 93/16081 | 8/1993 | WIPO . |
| WO 96/06601 | 3/1996 | WIPO . |

OTHER PUBLICATIONS

Grzycki et al., Acta Anat., 82(1), 91–96 (1972).
Urticaria and Physical Allergy, pp. 825–836, Fink, Jordan N. (1968).
Toxicon, vol. 29, No. 8, pp. 1033–1042, 1991.
Forbes, et al., J. Med. Chem. 36:1104–1107 (1993).
Leonard, B.E., Int'l. Clin. Pharm., 7:13–21 (1992).
Fludzinski, et al., J. Medicinal Chem., 29:2415–2418 (1986).
Kalkman, H.O., Life Sciences, 54:641–644 (1994).
Wainscott, et al., Molecular Pharmacology, 43:419–426 (1993).
Foguet, et al., Neuro Report 3, 345–348 (1992).
Cohen, et al., J. Pharm. & Exp. Therap., 233:75–79 (1985).
Cohen, et al., J. Pharm. & Exp. Therap., 232:770–774 (1984).
Clinschmidt, et al., J. Pharm. & Exp. Therap., 235:696–708 (1985).
Cohen, et al., Life Sciences, 38:1–5 (1985).

*Primary Examiner*—Phyllis G. Spivack
*Attorney, Agent, or Firm*—Arleen Palmberg

[57] ABSTRACT

This invention provides a method for the treatment or amelioration of the symptoms of venomous bites or stings which comprises administering to a mammal in need thereof one or more 5-HT$_2$ antagonists.

11 Claims, No Drawings

METHODS OF TREATING OR AMELIORATING THE SYMPTOMS OF VENOMOUS BITES AND STINGS

This application claims the benefit of U.S. Provisional Application 60/014,039, filed Mar. 25, 1996.

FIELD OF THE INVENTION

The present invention is directed to the use of 5-$HT_2$ antagonists for treating or ameliorating the symptoms of venomous bites or stings.

BACKGROUND OF THE INVENTION

Venomous bites and stings can cause a variety of reactions depending upon the source of the venom and the sensitivity of the individual or animal. In some cases, venom from a bite or sting can cause anaphylaxis, an immediate hypersensitivity which can be life-threatening. In other cases, certain venoms can cause cutaneous "local" reactions. Cutaneous local reactions can be characterized as 1) "non-allergic" reactions which are of limited size and duration or as 2) "allergic" or "large" local reactions which are typically larger in size and longer in duration. With regard to Hymenoptera venoms (bee, wasp, hornet and yellowjacket), "the non-allergic local reaction is a toxic response to venom constituents, while the large local reaction appears to be caused by an allergic reaction to venom proteins." See, D. N. Wright, Local Reactions To Stinging Insects (Hymenoptera), *Allergy Proc.* 11(1):23–28 Jan.–Feb. 1990).

Upon receiving a venomous bite or sting, a variety of symptoms can be exhibited due to the venom, including pruritus, erythema, urticaria, angioedema, soft tissue swelling, inflammation of the affected area and pain in the affected area.

When injected subcutaneously, many venoms from bites and stings induce extravasation from adjacent blood vessels. See, V. Cattell, Focal Mesangial Proliferative Glomerulonephritis In The Rat Caused By Habu Snake Venom: The Role Of Platelets, *British J. of Exp. Pathol.,* 60(2):201–208 (April 1979); In addition, the venoms induce platelet aggregation and mast cell degranulation, two components of inflammation along with extravasation. Serotonin release has also been associated with the injection of venoms. See, for instance, Y. Ozaki, et al, Mastoparan, A Wasp Venom, Activates Platelets Via Pertussis Toxin-Sensitive GTP-Binding Proteins, *Biochem. Biophys. Res. Commun.,* 170(2):779–85 (Jul. 31, 1990) and C. Wang, et al, Experimental Study of Chinese Agkistrodon Actus Venom In Activation Of Rabbit Platelets In Vivo, *Hua Hsi I Ko Ta Hsueh Hsueh Pao,* 25(1):38–40 (March 1994).

Since the discovery of serotonin (5-hydroxytryptamine, 5-HT) over four decades ago, the cumulative results of many diverse studies have indicated that serotonin plays a significant role in the functioning of the mammalian body, both in the central nervous system and in peripheral systems as well. Morphological studies of the central nervous system have shown that serotonergic neurons, which originate in the brain stem, form a very diffuse system that projects to most areas of the brain and spinal cord. R. A. O'Brien, *Serotonin in Mental Abnormalities,* 1:41 (1978); H. W. M. Steinbusch, Handbook of Chemical Neuroanatomy, Volume 3, Part II, 68 (1984); N. E. Anden, et al., *Acta Physiological Scandinavia,* 67:313 (1966). These studies have been complemented by biochemical evidence that indicates large concentrations of 5-HT exist in the brain and spinal cord. H. W. M. Steinbusch, supra.

With such a diffuse system, it is not surprising that 5-HT has been implicated as being involved in the expression of a number of behaviors, physiological responses, and diseases which originate in the central nervous system. These include such diverse areas as sleeping, eating, perceiving pain, controlling body temperature, controlling blood pressure, depression, schizophrenia, and other bodily states. R. W. Fuller, Biology of Serotonergic Transmission, 221 (1982); D. J. Boullin, Serotonin in Mental Abnormalities 1:316 (1978); J. Barchas, et al., *Serotonin and Behavior,* (1973).

Serotonin plays an important role in peripheral systems as well. For example, approximately 90% of the body's serotonin is synthesized in the gastrointestinal system, and serotonin has been found to mediate a variety of contractile, secretory, and electrophysiologic effects in this system. Serotonin may be taken up by the platelets and, upon platelet aggregation, be released such that the cardiovascular system provides another example of a peripheral network that can release and respond to serotonin. Given the broad distribution of serotonin within the body, it is understandable that tremendous interest in drugs that affect serotonergic systems exists. In particular, receptor-specific agonists and antagonists are of interest for the treatment of a wide range of disorders, including anxiety, depression, hypertension, migraine, compulsive disorders, schizophhrenia, autism, neurodegenerative disorders, such as Alzheimer's disease, Parkinsonism, and Huntington's chorea, and cancer chemotherapy-induced vomiting. M. D. Gershon, et al., The Peripheral Actions of 5-HYDROXYTRYPTAMINE, 246 (1989); P. R. Saxena, et al., *Journal of Cardiovascular Pharmacology,* 15:Supplement 7 (1990).

Serotonin produces its effects on cellular physiology by binding to specialized receptors on the cell surface. Multiple types of receptors exist for many neurotransmitters and hormones, including serotonin. The existence of multiple, structurally distinct serotonin receptors has provided the possibility that subtype-selective pharmacologic agents can be produced. The development of such compounds could result in new and increasingly selective therapeutic agents with fewer side effects, since activation of individual receptor subtypes may function to affect specific actions of the different parts of the central and/or peripheral serotonergic systems.

An example of such specificity can be demonstrated by using the vascular system as an example. In certain blood vessels, stimulation of certain 5-HT receptors on the endothelial cells produces vasodilation while stimulation of certain 5-HT receptors on the smooth muscle cells produces vasoconstriction.

Currently, the major classes of serotonin receptors (5-$HT_1$, 5-$HT_2$, 5-$HT_3$, 5-$HT_4$, 5-$HT_5$, 5-$HT_6$, and 5-$HT_7$) contain some fourteen to eighteen separate receptors that have been formally classified based on their pharmacological or structural differences. [For an excellent review of the pharmacological effects and clinical implications of the various 5-HT receptor types, see Glennon, et al., *Neuroscience and Behavioral Reviews,* 14:35 (1990).] discoveries.

One class of serotonin receptors is the 5-$HT_2$. Of this class, several subtypes are known to exist. These subtypes include 5-$HT_{2A}$, 5-$HT_{2B}$ and 5-$HT_{2C}$. The subtype 5-$HT_{2A}$ is located in many tissues, including but not limited to, the vascular smooth muscle, platelets, lung, CNS and gastrointestinal tract. This receptor is thought to be associated with several effects: for example, vasoconstriction, platelet aggregation, and bronchoconstriction. The 5-$HT_{2B}$ receptor is localized in the rat lung, stomach fundus, uterus, bladder, and colon. Interesting areas of 5-HT$_{2B}$ receptor localization in the human include, but are not limited to, the brain and blood vessels. Subtype 5-HT$_{2C}$ is located in the CNS with a high density in the choroid plexus.

Because of the widespread dissatisfaction with the current treatments for venomous bites and stings within the affected population, there exists a need for a more efficacious and safe treatment. The present invention provides such a treatment.

SUMMARY OF THE INVENTION

This invention provides a method for the treatment or amelioration of the symptoms of venomous bites or stings in a mammal which comprise administering to a mammal in need thereof an effective amount of one or more compounds having activity as 5-HT$_2$ antagonists.

DEFINITIONS

The terms and abbreviations used in the instant preparations and examples have their normal meanings unless otherwise designated. For example "°C." refers to degrees Celsius; "N" refers to normal or normality; "mmol" refers to millimole or millimoles; "g" refers to gram or grams; "ml" means milliliter or milliliters; "L" means liter or liters; "M" refers to molar or molarity; "MS" refers to mass spectrometry; "IR" refers to infrared spectroscopy; and "NMR" refers to nuclear magnetic resonance spectroscopy.

The term "sting" refers to an injury caused by the venom of an insect or other animal (biotoxin) introduced into the individual, together with the mechanical trauma caused by the organ responsible for its introduction.

The term "venom" refers to a poison, more specifically, a toxic substance normally secreted by an insect or other animal. As used herein, the term "venom" does not include substances which are considered to be neurotoxins. Examples of insects or other animal which are known to secrete venom include, but are not limited to, certain types of snakes, ants, jellyfish, hydra, man-of-war, stingrays, sea anemones, sea urchins, cone snails, spiders, scorpions, mosquitoes, bees, yellow jackets, hornets, wasps, gnats and flies.

"Inflammation" is a non-specific response of tissues to diverse stimuli or insults and results in the release of materials at the site of inflammation that induce pain. It is now recognized that mast cells, neutrophils, and T-cells are implicated in the pathophysiology of inflammatory skin conditions as well as in other physiological disorders.

DETAILED DESCRIPTION AND PREFERRED EMBODIMENTS

The methods of the present invention employ 5-HT$_2$ receptors. There are three members of the 5-hydroxytryptamine 2 (5-HT$_2$) family of 5-HT receptors, 5-HT$_{2A}$, 5-HT$_{2B}$ and 5-HT$_{2C}$ receptors. These receptors are G-protein linked receptors that are positively coupled to phosphoinositide metabolism, at least in the cloned versions of these receptors. These receptors share sequence homology and have the same pattern of introns and exons. Similarities in the specificity of the receptors for the ligands further indicates the commonalty of receptors in this family. Preferably, the methods of the present invention employ 5-HT$_{2B}$ receptors.

The present invention provides a method for the treatment or amelioration of the symptoms of venomous bites or stings which comprise administering to a mammal in need thereof an effective amount of one or more 5-HT$_2$ receptor antagonists. As noted, one or more 5-HT$_2$ antagonists are used in the present method. In one embodiment, only one 5-HT$_2$ antagonist is used. In some instances, the 5-HT$_2$ antagonist will have affinity for only one subtype of 5-HT$_2$ receptor (i.e., specificity for 5-HT$_{2A}$, 5-HT$_{2B}$, or 5-HT$_{2C}$). In other instances, the 5-HT$_2$ antagonist will have affinity for multiple subtypes of 5-HT$_2$ receptors (i.e., specificity for 5-HT$_{2A}$ and 5-HT$_{2B}$; 5-HT$_{2A}$ and 5-HT$_{2C}$; 5-HT$_{2B}$ and 5-HT$_{2C}$; or 5-HT$_{2A}$, 5-HT$_{2B}$ and 5-HT$_{2C}$). In an additional embodiment, multiple 5-HT$_2$ antagonists will be used. Each of these 5-HT$_2$ antagonists can have affinity for specific 5-HT$_2$ receptor subtypes, multiple 5-HT$_2$ receptor subtypes or can be a mixture of 5-HT$_2$ antagonists that have affinity for specific receptor subtypes and multiple receptor subtypes. A more preferred embodiment of the present invention provides methods for the treatment or amelioration of the symptoms of venomous bites or stings which comprise administering to a mammal in need thereof an effective amount of one or more 5-HT$_{2B}$ receptor antagonists.

Those of ordinary skill in the art will recognize that while the antagonists used in the present invention may have an affinity for one or more 5-HT$_2$ receptor subtypes, a certain amount of cross-reactivity with other 5-HT receptor classes can occur. A compound or composition is not precluded from being used in the present method simply because it has an affinity for one or more classes of 5-HT receptors.

In recent publications many different 5-HT$_2$ receptor antagonists which can be utilized in the present method have been described.

For instance, U.S. Pat. No. 5,428,036, incorporated herein by reference, describes a group of 5-HT$_2$ antagonists of Formula II:

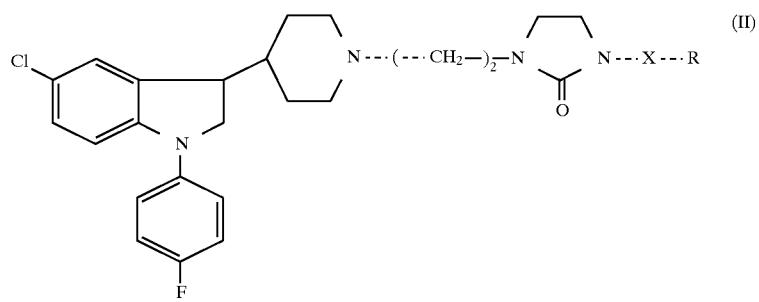

wherein X is selected from CO, CS or CH$_2$, and if X is CO or CS, R is selected from the group consisting of:

i) hydrogen, C$_1$–C$_{24}$ alkyl, C$_2$–C$_{24}$ alkenyl, C$_3$–C$_8$ cycloalkyl, C$_3$–C$_8$ cycloalkenyl or C$_4$–C$_{32}$ cycloalk(en)ylalk(en)yl, optionally substituted with one or two hydroxy groups, or phenyl optionally substituted with one or more substituents selected from the group consisting of halogen, trifluoromethyl, C$_1$–C$_4$ alkyl, C$_1$–C$_4$ alkoxy, C$_1$–C$_4$ alkylthio, acyloxy, or cyano; or ii) YR$^1$, wherein Y is O or S and R$^1$ is selected from the substituents defined for R under i) above; and iii) NR$^2$R$^3$, wherein R$^2$ and R$^3$ independently are selected from the substituents defined for R under i) above or R$^2$ and R$^3$ are combined to form a four to eight member heterocyclic ring containing from one to three nitrogen atoms and from zero to three oxygen or sulfur atoms; or if X is CH$_2$, R is selected from the groups consisting of:

iv) a group YR$^1$ as defined in ii);

v) a group NR$^2$R$^3$ as defined in iii); or vi) a group OC(O)R$^4$, wherein R$^4$ is as defined for R$^1$; and pharmaceutically acceptable salts thereof.

Another group of 5-HT$_2$ antagonists include the compounds described in U.S. Pat. No. 5,229,382, incorporated herein by reference, which are of the general Formula III:

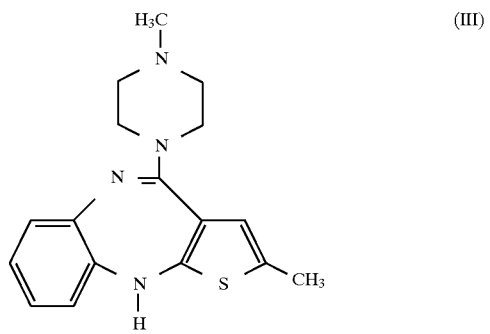

Still another group of 5-HT$_2$ antagonists are those in U.S. Pat. No. 5,457,115, incorporated herein by reference, which describes antagonists of the Formula IV:

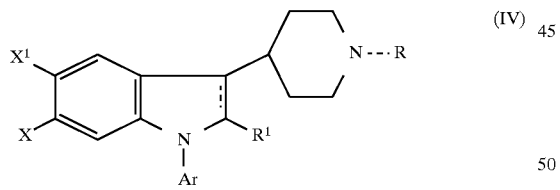

where Ar is one of a phenyl group, a phenyl group substituted with at least one substituent selected from halogen, lower alkyl, lower alkoxy, hydroxy, trifluoromethyl, and cyano, and a hetero aromatic group selected from 2-thienyl, 3-thienyl, 2-furanyl, 3-furanyl, 2-oxazolyl, 2-imidazolyl, 2-pyridyl, 3-pyridyl, and 4-pyridyl; each dotted line is an optional double bond; X and X$^1$ are independently selected from the group consisting of hydrogen, halogen, lower alkyl, lower alkoxy, hydroxy, lower alkylthio, lower alkylsulfonyl, lower alkylamino, lower dialkylamino, cyano, trifluoromethyl, and trifluoromethylthio; or X and X$^1$ are taken together to form a 5 to 7 membered carbocyclic ring; R$^1$ is selected from the group consisting of hydrogen, lower alkyl and alkyl substituted with one or two hydroxy groups; with the proviso that when X is hydrogen or fluoro then R$^1$ cannot be hydrogen; R is a substituent having the formula:

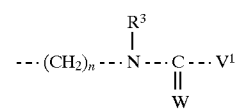

wherein n is an integer from 2–6 inclusive; W is oxygen or sulfur; V$^1$ is selected from OR$^4$, SR$^5$, CHR$^6$R$^7$, and NR$^8$R$^9$; wherein R$^3$ to R$^9$ are independently selected from the group consisting of hydrogen, lower alkyl, lower alkenyl, cycloalkyl, lower alkyl substituted with one or two hydroxyl groups; and lower alkenyl substituted with one or two hydroxyl groups; and pharmaceutically acceptable acid addition salts or prodrugs thereof.

An even further group of 5-HT$_2$ antagonists which can be utilized in the present method include those in U.S. Pat. No. 5,480,885, incorporated herein by reference, which describes antagonists of the Formula V:

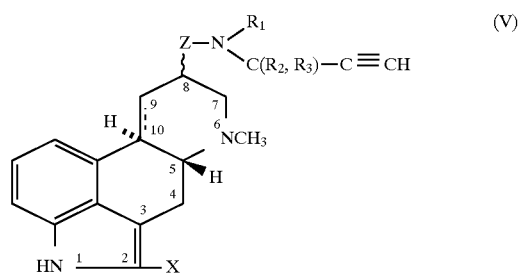

wherein R$_1$, R$_2$ and R$_3$ independently represent a hydrogen atom or a straight-chain or branched-chain C$_1$–C$_6$ alkyl group, X represents a hydrogen or a halogen atom;

Z represents a carbonyl or methylene group and C9–C10 represents a single or a double bond, racemates and acid addition salts thereof.

An even further group of 5-HT$_2$ antagonists which can be utilized in the present method include those in U.S. Pat. No. 4,563,461, incorporated herein by reference, which describes compounds of the Formula VI:

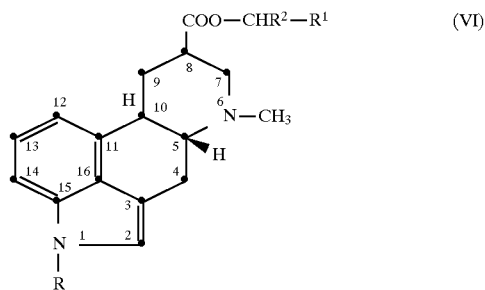

wherein R is C$_{1-3}$ alkyl or allyl, R$^1$ is C$_{1-3}$ hydroxyalkyl or C$_{1-3}$ dihydroxyalkyl and R$^2$ is H or CH$_3$, or a pharmaceutically acceptable salt thereof.

The above groups of compounds are only illustrative of the 5-HT$_2$ receptor antagonists which can be utilized. This listing of groups of compounds is not meant to be comprehensive, the methods of the present invention may employ any 5-HT$_2$ receptor antagonist and is not limited to any particular class of compound.

A more preferred class of antagonists are the 5-HT$_2$ receptor antagonists of Formula VII:

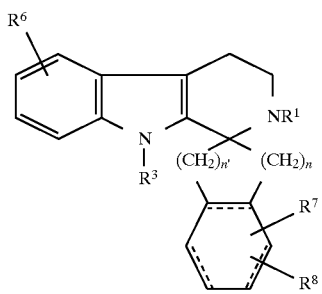

(VII)

wherein $R^1$ is hydrogen or $C_1$–$C_3$ alkyl;

$R^3$ is hydrogen or $C_1$–$C_3$ alkyl;

$R^6$ is selected from the group consisting of hydrogen, $C_1$–$C_6$ alkyl, $C_2$–$C_6$ alkenyl, halo, halo($C_1$–$C_6$)alkyl, halo($C_2$–$C_6$)alkenyl, $COR^5$, $C_1$–$C_{10}$ alkanoyl, $CO_2R^{5'}$, ($C_1$–$C_6$ alkyl)$_m$amino, $NO_2$, —$SR^5$, and $OR^5$;

$R^7$ and $R^8$ are independently selected from the group consisting of hydrogen, $C_1$–$C_6$ alkyl, $C_2$–$C_6$ alkenyl, $NO_2$, halo, halo($C_1$–$C_6$)alkyl, halo($C_2$–$C_6$)alkenyl, $COR^5$, $C_1$–$C_{10}$ alkanoyl, $C_7$–$C_{16}$ arylalkyl, $CO_2R_{5'}$, ($C_1$–$C_6$ alkyl)$_m$amino, —$SR^5$, and $OR^5$;

n is 1, 2, or 3;

n' is 1, 2, or 3;

m is 1 or 2;

$R^5$ is independently hydrogen or $C_1$–$C_4$ alkyl;

$R^{5'}$ is $C_1$–$C_4$ alkyl;

— is optionally a bond;

a pharmaceutically acceptable salt or solvate thereof.

Examples of compounds of Formula VII include but are not limited to: spiro-9,9[2-(3,4-dichloro)-1,2,3,4-tetrahydronaphthyl]-5-methoxy-1,2,3,9-tetrahydro-8H-pyrido indole, spiro-9,9[2-(3,4-dimethoxy)-1,2,3,4-tetrahydronaphthyl]-5-methyl-1,2,3,9-tetrahydro-8H-pyrido indole, spiro-9,9[2-(3,4-diethoxy)-1,2,3,4-tetrahydronaphthyl]-5-methyl-1,2,3,9-tetrahydro-8H-pyrido indole, spiro-9,9[2-(3,5-dichloro)-1,2,3,4-tetrahydronaphthyl]-5-dimethylamino-1,2,3,9-tetrahydro-8H-pyrido indole, spiro-9,9[2-(3-fluoro,4-chloro)-1,2,3,4-tetrahydronaphthyl]-5-ethyl-1,2,3,9-tetrahydro-8H-pyrido indole, spiro-9,9[2-(3,4-dimethoxy)-1,2,3,4-indole, spiro-9,9[2-(3,4-dimethoxy)-1,2,3,4-tetrahydronaphthyl]-5-bromo-1,2,3,9-tetrahydro-8H-pyrido indole, spiro-9,9[2-(3,4-dimethoxy)-1,2,3,4-tetrahydronaphthyl]-5-chloro-1,2,3,9-tetrahydro-8H-pyrido indole.

The synthesis of these compounds is described in co-pending U.S. Provisional Patent Application Serial No. 60/014,119, Attorney Docket No. P-10656, filed Mar. 25, 1996, incorporated herein by reference. The syntheses of typical compounds from this class, including six specific examples, are detailed infra.

The compounds of Formula VII can be prepared using chemical processes that are understood in the art. The examples are illustrative only, and are not intended to limit the scope of the invention.

Indole Starting Materials

The indole starting materials (1a, 1b, and 1c) infra. were purchased (1a), prepared according to Bartoli's procedure (1b) [Bartoli, G. et al. *Tetrahedron Lett.*, 1989, 30, 2129] or (1c) synthesized from 2-Iodo-4,6-dimethylaniline (5'''). The process is illustrated by the following Scheme:

Scheme IV

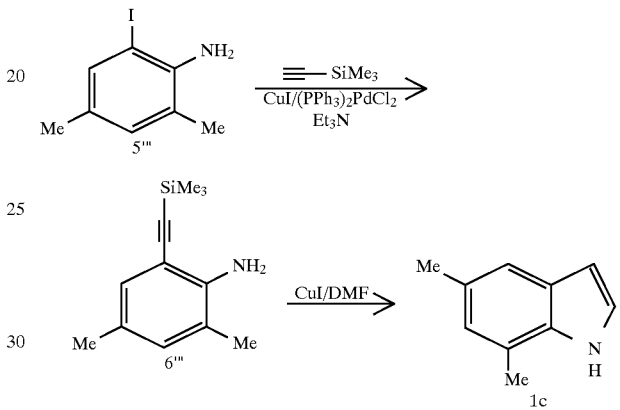

The 2-Iodo-4,6-dimethylaniline (5''') synthesis can be completed as follows: To a suspension of 5''' (24 mmol.), CuI (0.05 equiv.) and $(PPh_3)_2PdCl_2$ (0.05 equiv.) in 30 ml of dry triethylamine under Ar. atmosphere was added trimethylsilylacetylene (1.1 equiv.) and the resulting mixture was stirred for 3 hours. Then, the solvent was eliminated under vacuum and the residue purified by flash chromatography using hexane/ethyl acetate (3:1) as eluent to yield 6''' in quantitative yield. A slurry of 61''' (23 mmol.) and CuI (2 equiv.) in 50 ml of dry dimethyl formamide was heated for 2.5 h. under Ar. atmosphere at 100° C. After cooling down to room temperature the reaction mixture was filtered off and the solid washed twice with ether (20 ml.). The organic phase was washed with water (3×50 ml.), dried over $Na_2SO_4$ and the solvent evaporated to dryness. The crude product was purified by flash chromatography using hexane/ethyl acetate (3:1) as eluent to afford 1c (1.5 g., 45%).

EXAMPLE 1

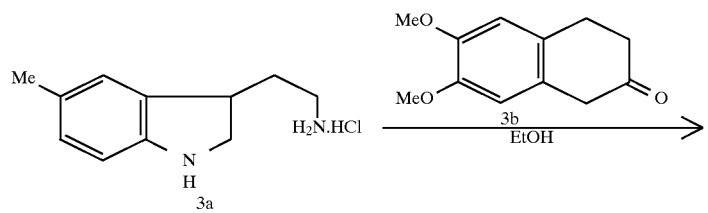

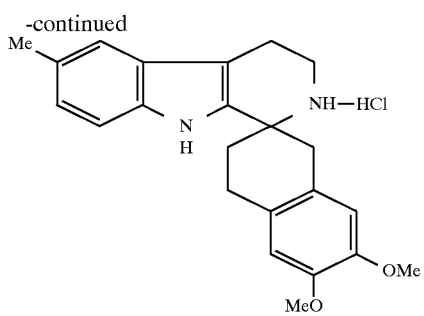

A suspension of the corresponding tryptamine hydrochloride (3a) (1 gram) and the corresponding dimethoxytetralone (3b) (1 gram) in ethanol (10 ml.) was refluxed during 128 h. After this time the reaction mixture was allowed to reach room temperature and filtered off. The crude solid was washed and dried. Melting point 261° C.

|   | Theory | Found |
|---|--------|-------|
| C | 69.25  | 69.34 |
| H | 6.82   | 6.97  |
| N | 7.02   | 6.98  |

EXAMPLE 2

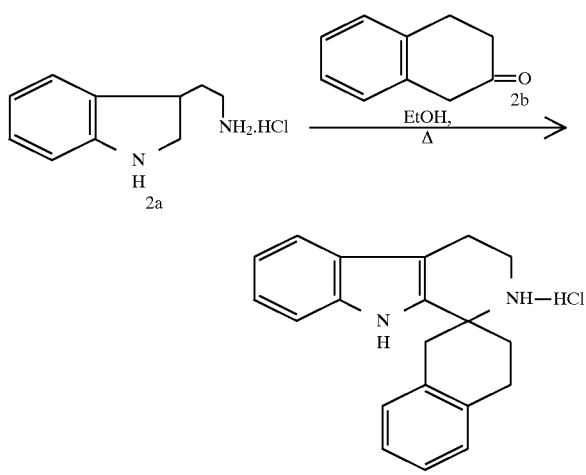

A suspension of the corresponding tryptamine hydrochloride (2a) (575 mg) and the corresponding ketone (2b) (464 mg) in ethanol (10 ml.) was refluxed during 128 h. After this time the reaction mixture was allowed to reach room temperature and filtered off. The crude solid was washed and dried.

Yield: 525 mg

|   | Theory | Found |
|---|--------|-------|
| C | 74.43  | 74.36 |
| H | 6.84   | 6.84  |
| N | 8.27   | 8.25  |

MS: 301

EXAMPLE 3

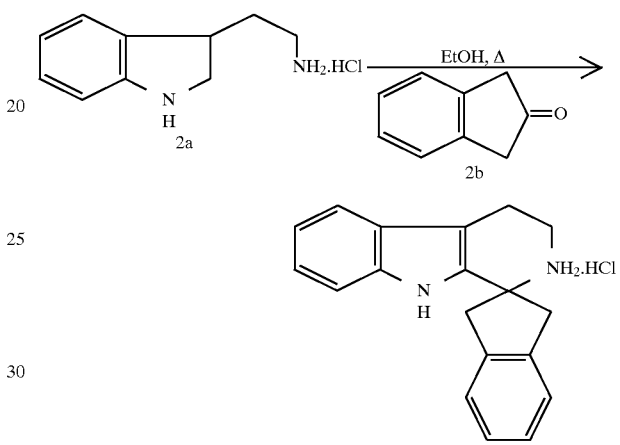

A suspension of the corresponding tryptamine hydrochloride (2a) (500 mg) and the corresponding ketone (2b) (396 mg) in ethanol (10 ml.) was refluxed during 72 h. After this time the reaction mixture was cooled to about 0° C. and filtered off. The crude solid was washed and dried.

Yield: 262 mg

MS: 274

EXAMPLE 4

A suspension of the corresponding tryptamine hydrochloride (4a) (500 mg) and the corresponding ketone (4b) (396 mg) in ethanol (10 ml.) was refluxed during 72 h. After this time the reaction mixture was cooled to about 0° C. for about 24 hours and filtered off. The crude solid was washed and dried.

Submitted for mass spectral analysis and found mi of 274.

EXAMPLE 5

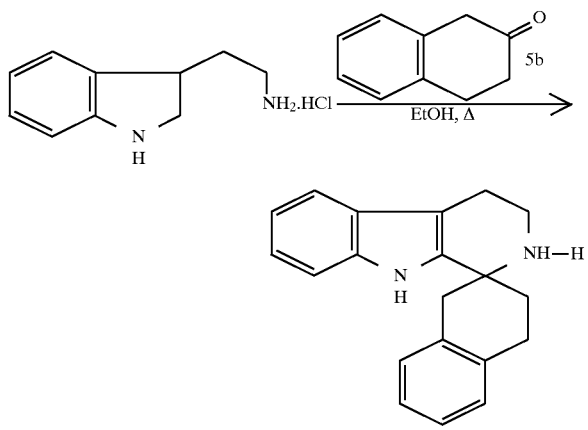

A suspension of the corresponding tryptamine hydrochloride (5a) (500 mg) and the corresponding ketone (5b) (397 uL) in ethanol (10 ml.) was refluxed during 72 h. After this time the reaction mixture was cooled to about 0° C. for 14 hours and filtered off. The crude solid was washed and dried.

Yield: 630 mg

|   | Theory | Found |
|---|--------|-------|
| C | 73.95  | 73.32 |
| H | 6.52   | 6.73  |
| N | 8.62   | 8.59  |

MS: 288

EXAMPLE 6

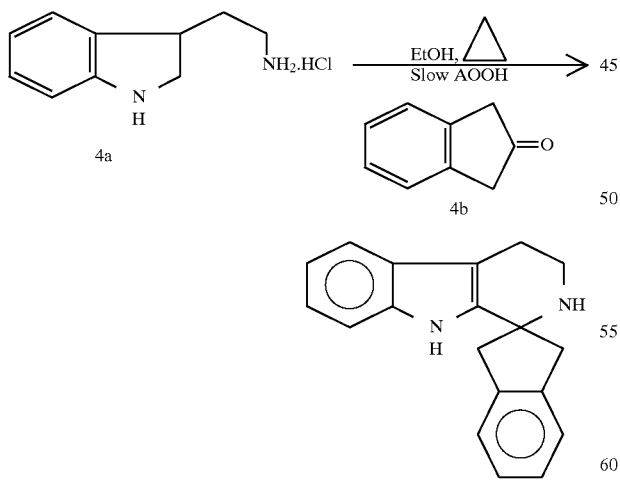

A suspension of the corresponding tryptamine hydrochloride (4a) (1 g) and the corresponding ketone (4b) (800 mg) in ethanol (10 ml.) was refluxed during 72 h. After this time the reaction mixture was cooled to about 0° C. for about 24 hours and filtered off. The crude solid was washed and dried.

Yield: 550 mg

|   | Theory | Found |
|---|--------|-------|
| C | 70.67  | 70.88 |
| H | 7.06   | 7.16  |
| N | 7.85   | 7.88  |

An additional preferred class of 5-HT$_2$ receptor antagonists are those compounds described in WO 95/24200, incorporated herein by reference, which are of Formula I:

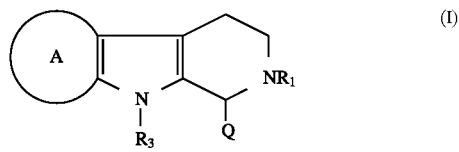

wherein
  Q is hydrogen or $(CHR_2)R_4$;
  $R_1$ is hydrogen or $C_1$–$C_3$ alkyl;
  $R_2$ is hydrogen or $C_1$–$C_3$ alkyl;
  $R_3$ is hydrogen or $C_1$–$C_3$ alkyl;
  $R_4$ is $C_5$–$C_8$ cycloalkyl, substituted $C_5$–$C_8$ cycloalkyl, $C_5$–$C_8$ cycloalkenyl, substituted $C_5$–$C_8$ cycloalkenyl, bicyclic or substituted bicyclic;
  A is selected from the group consisting of

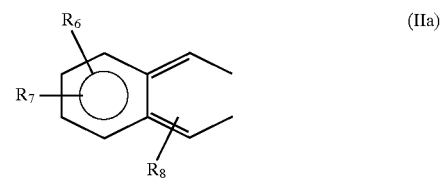

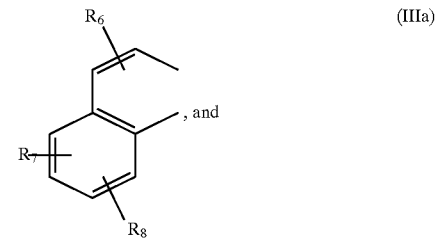

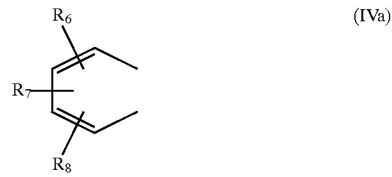

wherein,
  $R^6$ and $R^7$ are, independently, hydrogen, $C_1$–$C_6$ alkyl, $C_2$–$C_6$ alkenyl, halo, halo($C_1$–$C_6$)alkyl, halo($C_2$–$C_6$) alkenyl, $COR_5$', $C_1$–$C_{10}$ alkanoyl, $CO_2R_5$', $(C_1$–$C_6$ alkyl)$_m$ amino, $NO_2$, —$SR_5$, or $OR_5$;
  m is 1 or 2;
  $R_5$ is independently hydrogen or $C_1$–$C_4$ alkyl;
  $R_5$' is $C_1$–$C_4$ alkyl;
  $R_8$ is independently selected from the group consisting of an $R_6$ group, substituted $C_3$–$C_8$ cycloalkyl, $C_3$–$C_8$ cycloalkyl, $C_3$–$C_8$ cycloalkyl-($C_1$–$C_3$)alkyl, $C_5$–$C_8$ cycloalkenyl, substituted $C_5$–$C_8$ cycloakenyl, $C_5$–$C_8$ cycloalkenyl-($C_1$–$C_3$)alkyl, $C_7$–$C_{16}$ arylalkyl; or R<sub>6</sub> and R<sub>7</sub> together with the carbon atoms of group A form a 5- to 8-member carbon ring;
or a pharmaceutically acceptable salt or solvate thereof.

Examples of compounds of Formula I include but are not limited to: 8-methyl-1-[3,4-dimethoxyphenyl)methyl]1,2,3,4-tetrahydro-9H-pyrido[3,4-b]indole, 8-bromo-1-[3,4-dimethoxyphenyl)methyl]-1,2,3,4-tetrahydro-9H-pyrido[3,4-b]indole hydrochloride, 6,8-dibromo-1-[3,4-dimethoxyphenyl)methyl]-1,2,3,4-tetrahydro-9H-pyrido[3,4-b]indole; 6-methyl-8-bromo-1-[3,4-dimethoxyphenyl)-methyl]-1,2,3,4-tetrahydro-9H-pyrido[3,4-b]indole hydrochloride; 8-methoxy-1-[3,4-dimethoxyphenyl)methyl]-1,2,3,4-tetrahydro-9H-pyrido[3,4-b]indole; 6,8-difluoro-1-[(3,4-dimethoxyphenyl)-methyl]-1,2,3,4-tetrahydro-9H-pyrido[3,4-b]indole; 7-methyl-8-bromo-1-[3,4-dimethoxyphenyl)-methyl]-1,2,3,4-tetrahydro-9H-pyrido[3,4-b]indole hydrochloride; 6-(1,1-dimethylethyl)-1-[(3,4-dimethoxyphenyl) methyl]1,2,3,4-tetrahydro-1-9H-pyrido[3,4b]indole hydrochloride; 5-fluoro-6-methyl-1-[(3,4-dimethoxyphenyl)-methyl]-1,2,3,4-tetrahydro-9H-pyrido[3,4-b]indole; 7,8,9,10-tetrahydro-10-[(3,4-dimethoxyphenyl)methyl]-11H-benzo[g]pyrido[3,4-b]indole; 6-cyclohexyl-1-[(3,4-dimethoxyphenyl)-methyl]-1,2,3,4-tetrahydro-9H-pyrido[3,4-b]indole hydrochloride; 5,8-dimethyl-1,2,3,4-tetrahydro-1-[(3,4-dimethoxyphenyl)methyl]-9H-pyrido[3,4b]indole hydrochloride; 6-(1-methylethyl)-1,2,3,4-tetrahydro-1-[(3,4-dimethoxyphenyl)methyl]-9H-pyrido[3,4b]indole; 6,8-dimethyl-1,2,3,4-tetrahydro-1-[(3,4-dimethoxyphenyl)methyl]-9H-pyrido[3,4b]indole hydrochloride; 5,7-dimethyl-1,2,3,4-tetrahydro-1-[(3,4-dimethoxyphenyl)methyl]- 9H-pyrido[3,4b]indole hydrochloride; 6,7-dimethyl-1,2,3,4-tetrahydro-1-[(3,4-dimethoxyphenyl)methyl]-9H-pyrido[3,4b]indole; 6-ethyl-1,2,3,4-tetrahydro-1-[(3,4-dimethoxyphenyl)methyl]-9H-pyrido[3,4b]indole; 6-bromo-1,2,3,4-tetrahydro-1-[(3,4-dimethoxyphenyl)methyl]-9H-pyrido[3,4b]indole; 7,8-dimethyl-1,2,3,4-tetrahydro-1-[(3,4-dimethoxyphenyl)methyl]-9H-pyrido[3,4b]indole hydrochloride; 6-methyl-1,2,3,4-tetrahydro-1-[(3,4-dimethoxyphenyl)methyl]-9H-pyrido[3,4b]indole hydrochloride; 6-methyl-1-[(3,4,5-trimethoxyphenyl)-methyl]-1,2,3,4-tetrahydro-9H-pyrido[3,4-b]indole hydrochloride; 6-methyl-1-[(2,3,4-trimethoxyphenyl)methyl]-1,2,3,4-tetrahydro-9H-pyrido[3,4-b]indole hydrochloride; 6-methyl-1-[(2-methoxyphenyl)methyl]-1,2,3,4-tetrahydro-9H-pyrido[3,4-b]indole hydrochloride; 6-methyl-1-[(2,4-dimethoxyphenyl)methyl]-1,2,3,4-tetrahydro-9H-pyrido[3,4-b]indole hydrochloride; 6-methyl-1-[(2,5-dimethoxyphenyl)methyl]-1,2,3,4-tetrahydro-9H-pyrido[3,4-b]indole hydrochloride; 6-methyl-1-[(2,4,5-trimethoxyphenyl)methyl]-1,2,3,4-tetrahydro-9H-pyrido[3,4-b]indole hydrochloride; 6-(1-methylethyl)-1-[(2,3,4-trimethoxy-phenyl)methyl]-1,2,3,4-tetrahydro-9H-pyrido[3,4-b]indole hydrochloride; 6-methyl-1-[(3,4-dimethoxy-5-nitrophenyl)methyl]-1,2,3,4-tetrahydro-9H-pyrido[3,4-b]indole hydrochloride; 6-methyl-1-[(3-iodo-4,5-dimethoxy-phenyl)methyl]-1,2,3,4-tetrahydro-9H-pyrido[3,4-b]indole; 6-methyl-1-[(3,4-dimethoxy-5-amino-phenyl)-methyl]-1,2,3,4-tetrahydro-9H-pyrido[3,4-b]indole dihydrochloride; 6-methyl-1-[(3-methoxy-4-propoxyphenyl)-methyl]-1,2,3,4-tetrahydro-9H-pyrido[3,4-b]indole; 6-methyl-1-[(4-dimethylaminophenyl)methyl]-1,2,3,4-tetrahydro-9H-pyrido[3,4-b]indole dihydrochloride; 6-methyl-1-[(4-dibutylaminophenyl)methyl]-1,2,3,4-tetrahydro-9H-pyrido[3,4-b]indole dihydrochloride; 6-methyl-1-[(3-fluoro-4-methoxyphenyl)-methyl]-1,2,3,4-tetrahydro-9H-pyrido[3,4-b]indole hydrochloride; 6-methyl-1-[(3,4-dimethylphenyl)methyl]-1,2,3,4-tetrahydro-9H-pyrido[3,4-b]indole hydrochloride; 6-methyl-1-[(2-chloro-3,4-dimethoxyphenyl)-methyl]-1,2,3,4-tetrahydro-9H-pyrido[3,4-b]indole hydrochloride; 6-methyl-1-[(2-chloro-3-methoxy-4-hydroxyphenyl)methyl]-1,2,3,4-tetrahydro-9H-pyrido[3,4-b]indole hydrochloride; 5-fluoro-6-methyl-1-[(2-chloro-3,4-dimethoxyphenyl)methyl]-1,2,3,4-tetrahydro-9H-pyrido[3,4-b]indole hydrochloride; 6-methyl-1-(cyclohexylmethyl)-1,2,3,4-tetrahydro-9H-pyrido[3,4-b]indole hydrochloride; 6-methyl-1-[(2-bromo-3,4-dimethoxyphenyl)-methyl]-1,2,3,4-tetrahydro-9H-pyrido[2,4-b]indole; and 6-iodo-1-[(3,4-dimethoxyphenyl)-methyl]-1,2,3,4-tetrahydro-9H-pyrido[3,4-b]indole hydrochloride.

EXAMPLE 7

Preparation of 6-methyl-1-[(2-chloro-3,4-dimethoxyphenyl)methyl]-1,2,3,4-tetrahydro-9H-pyrido[3,4-b]indole hydrochloride

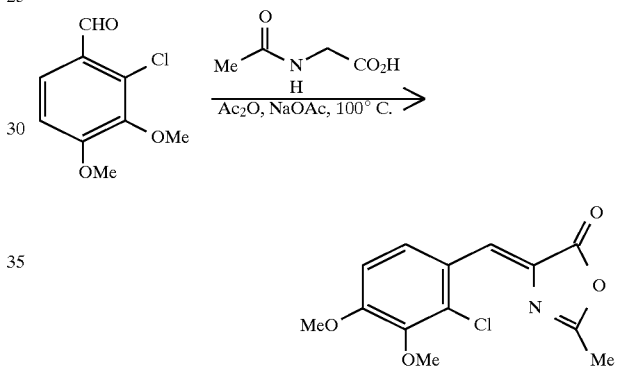

A solution of 2-chloro-3,4-dimethoxybenzaldehyde (10.45 g), N-acetylglycine (11.9 g, 0.10 mol.) and sodium acetate (8.4 g, 0.1 mol) in acetic anhydride (100 mL) was heated to 100° C. for 2 hours. The reaction mixture was cooled to ambient temperature poured onto ice (300 mL) with stirring. The product was isolated by filtration, washed with water (3×50 mL) and diethyl ether (3×50 mL) and dried under reduced pressure (5.26 g).

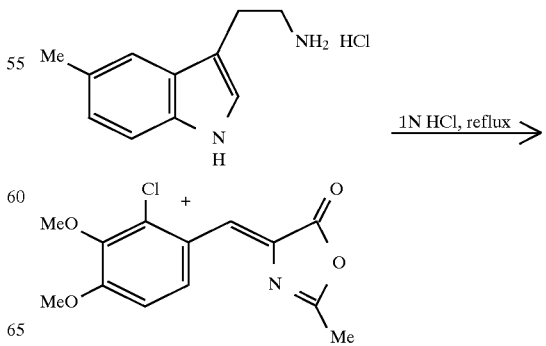

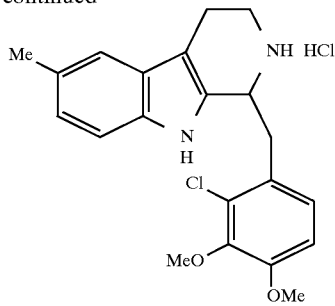

A suspension of azalactone prepared above (1.34 g, 4.76 mmol.) and 5-methyltryptamine hydrochloride (1.0 g, 4.75 mmol.) in 1N HCl (30 mL) was heated to reflux for 24 hours under nitrogen atmosphere. The reaction mixture was cooled to ambient temperature and the crude product isolated by filtration. The solid was triturated with ethanol and washed with diethyl ether. The product was isolated by filtration (1.19 g). m/e=370, mp. 244° C. (dec.).

| Analysis | Calculated | Found |
|---|---|---|
| C | 61.92 | 61.67 |
| H | 5.94 | 5.94 |
| N | 6.88 | 6.94 |

EXAMPLE 8

Preparation of 6-methyl-1-[(2-bromo-3,4-dimethoxyphenyl)methyl]-1,2,3,4-tetrahydro-9H-pyrido[3,4-b]indole Example 8 was prepared in the same manner as described in Example 7 with the following exception: 2-bromo-3,4-dimethoxybenzaldehyde was used instead of 2-chloro-3,4-dimethoxybenzaldehyde as starting material. The final compound produced

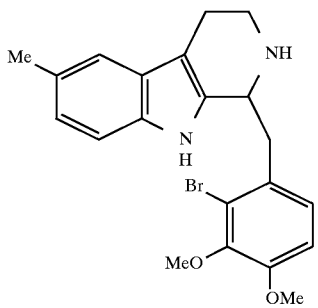

had a yield of 79.2%; M/I 416, 414; and mp 272°–4° C.

| Analysis | Calculated | Found |
|---|---|---|
| C | 55.83 | 55.57 |
| H | 5.35 | 5.36 |
| N | 6.20 | 6.09 |

EXAMPLE 9

Preparation of 6-iodo-1-[(3,4-dimethoxyphenyl)-methyl]-1,2,3,4-tetrahydro-9H-pyrido[3,4-b]indole hydrochloride Example 9 was prepared in the same manner as Example 7 with the following exceptions: 3,4-dimethoxybenzaldehyde was used instead of 2-chloro-3,4-dimethoxybenzaldehyde and 5-iodo-tryptamine instead of 5-methyl-tryptamine as starting materials. Upon completion of the reaction, the mixture was neutralized with aqueous potassium carbonate solution and extracted with chloroform. The combined chloroform phases were dried over anhydrous sodium carbonate and concentrated under reduced pressure. The product was purified by chromatography on silica gel, eluting with 2% methanol in chloroform. Fractions containing product were pooled and concentrated. The residue was dissolved in diethyl ether and was treated with gaseous HCl. The resulting HCl salt was isolated by filtration and dried under reduced pressure. The final compound produced

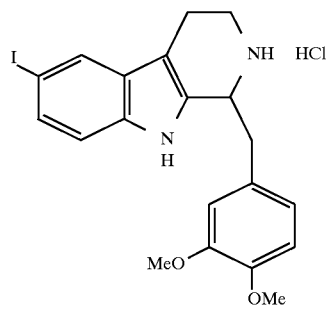

had a yield of 31.3%; M/I 448; and mp 270°–3° C.

| Analysis | Calculated | Found |
|---|---|---|
| C | 49.55 | 49.62 |
| H | 4.57 | 4.51 |
| N | 5.78 | 5.66 |

The biological efficacy of a compound believed to be effective as a $5\text{-HT}_2$ receptor antagonist may be confirmed by first employing an initial screening assay which rapidly and accurately measures the binding of the test compound to the $5\text{-HT}_2$ receptor. Once the binding of the test compound is established, the in vivo activity of the test compound on the receptor is established. Assays useful for evaluating $5\text{-HT}_2$ antagonist are well known by those skilled in the art.

$5\text{-HT}_{2B}$ Receptor Binding Activity

The ability of a compound to bind to a $5\text{-HT}_{2B}$ receptor was measured using standard procedures such as that listed below.

Assay Procedure

Certain compounds and intermediates of the present invention are useful for modulating $5\text{-HT}_{2B}$ receptors. The compounds which are most useful for binding a $5\text{-HT}_{2B}$ receptor can be identified using the following procedures. Further, a useful in vivo model for demonstrating $5\text{-HT}_{2B}$ activity is provided infra.

Radioligand Binding Studies for $5\text{-HT}_{2B}$

Membrane preparation from transformed cells: Suspension cells expressing the cloned rat $5\text{-HT}_{2B}$ receptor were harvested by centrifugation at 2,200×g for 15 min at 4° C. J. Kursar, et al, *Mol. Pharmacol.*, 42:549–557 (1992). Membranes for the binding assays were prepared by vortexing the pellet in 50 mM Tris-HCl, pH 7.4 (0.5×10⁹ cells/30 ml). The tissue suspension was then centrifuged at 39,800×g for 10 min at 4° C. This procedure was repeated for a total of three washes, with a 10 minute incubation at 37° C. between the first and second wash. The final pellet was homogenized in 67 mM Tris-HCl, pH 7.4 (at 20–40 and 12.5 million cells/ml, original cell number, for cells expressing low and relatively high levels of the $5\text{-HT}_{2B}$ receptor, respectively) using a Tissumizer (Tekmar, Cincinnati, Ohio), setting 65 for 15 seconds.

[³H]5-HT binding studies: Binding assays were automated using a Biomek 1000 (Beckman Instruments, Fullerton, Calif.) and were performed in triplicate in 0.8 ml total volume. Membrane suspension, 200 μl, (0.04–0.27 mg protein) and 200 μl of drug dilution in water were added to 400 μl of 67 mM Tris-HCl, pH 7.4, containing [³H]5-HT, pargyline, $CaCl_2$, and L-ascorbic acid. Final concentrations of pargyline, $CaCl_2$ and L-ascorbic acid were 10 μM, 3 mM and 0.1%, respectively. Tubes were incubated at 37° C. for 15 min or at 0° C. for 2 hours (binding equilibria were verified for both of these conditions), then rapidly filtered using a Brandel cell harvester (Model MB-48R; Brandel, Gaithersburg, Md.) through Whatman GF/B filters which had been presoaked in 0.5% polyethylenimine and precooled with ice-cold 50 mM Tris-HCl, pH 7.4. The filters were then washed rapidly four times with one ml ice-cold 50 mM Tris-HCl, pH 7.4. The amount of [³H]5-HT trapped on the filters was determined by liquid scintillation spectrometry (Ready Protein and Beckman LS 6000IC, Beckman Instruments, Fullerton, Calif.). For the saturation experiments, actual free radioligand concentrations were determined by sampling the supernatant of parallel saturation experiments in which bound radioactivity had been separated by centrifugation. The concentration of [³H]5-HT ranged from 0.02 to 5 nM and 0.6 to 63 nM for saturation experiments incubated at 0° C. and 37° C., respectively. 5-HT, 10 μM, or 1-naphthylpiperazine (1-NP), 10 μM, defined nonspecific binding. For competition experiments, six to twelve concentrations of displacing drugs were used, spanning six log units, and the final concentration of [³H] 5-HT was 2 nM. Protein was determined by the method of Bradford, using bovine serum albumin as the standard. M. M. Bradford, *Anal. Biochem.*, 72: 248–254 (1976).

Statistical Analysis

The $K_d$ and $B_{max}$ values from the saturation assays were determined for best fit to a one-site or a two-site binding model using a partial F-test. A. De Lean, et al, *Mol. Pharmacol.*, 21:5–16 (1981). The following equation was used for a one-site binding model, $$\text{Bound} = \frac{B_{max} \times [L]}{K_d + [L]}$$

where Bound=amount of [³H]5-HT specifically bound, $B_{max}$=maximum number of binding sites, $K_d$=equilibrium dissociation constant and [L]=free concentration of [³H]5-HT, or a two-site binding model, $$\text{Bound} = \frac{B_{max1} \times [L]}{K_{d1} + [L]} + \frac{B_{max2} \times [L]}{K_{d2} + [L]}$$

where Bound=amount of [³H]5-HT specifically bound, $B_{max1}$=maximum number of high affinity binding sites, $B_{max2}$=maximum number of low affinity binding sites, $K_{d1}$=equilibrium dissociation constant for the high affinity site, $Kd_2$=equilibrium dissociation constant for the low affinity site and [L]=free concentration of [³H]5-HT. The $IC_{50}$ values from the competition assays, the binding parameters for the $IP_3$ standard curve and the $EC_{50}$ and $E_{max}$ values from the $IP_3$ assays were determined by nonlinear regression analysis of four parameter logistic equations (Systat, Systat Inc, Evanston, Ill.). A. De Lean, et al, *Mol. Pharmacol.*, 21:5–16 (1981). The $IC_{50}$ values were converted to $K_i$ values using the Cheng-Prusoff equation. Y. Cheng, et al, *Biochem. Pharmacol.*, 22:3099–3108 (1973).

Assay Methods 5-$HT_{2B}$ in vitro

Male Wistar rats (150–375 g; Laboratory Supply, Indianapolis, Ind.) were sacrificed by cervical dislocation, and longitudinal section of the stomach fundus were prepared for in vitro examination. Four preparations were obtained from one rat fundus. Ring preparations of the extracted jugular vein were prepared as described by Hooker; Blood Vessels, 14:1 (1977) and M. L. Cohen, *J. Pharamcol. Exp. Ther.*, 227:327 (1983). Tissues were mounted in organ baths containing 10 mL of modified Krebs solution of the following composition (millimolar concentrations): NaCl, 118.2; KCl, 4.6; $CaCl_2.H_2O$, 1.6; $KH_2PO_4$, 1.2; $MgSO_4$, 1.2; dextrose, 10.0; and $NaHCO_3$, 24.8. Tissue bath solutions were maintained at 37° C. and equilibrated with 95% $O_2$ and 5% $CO_2$. Tissues were placed under optimum resting force (4 g) and were allowed to equilibrate for approximately 1 hour before exposure to the test compound. Isometric contractions were recorded as changes in grams of force on a Beckman Dynograph with Statham UC-3 transducers.

Determination of Apparent Antagonist Dissociation Constant

Noncumulative contractile concentration-response curves for serotonin in the fundus and cumulative concentration response curves in the jugular vein were obtained by a stepwise increase in concentration after washing out the preceding concentrations every 15–20 minutes. Each agonist concentration remained in contact with the tissue for approximately 2 minutes and maximum response to each compound concentration was measured $ED_{50}$ values were taken as the concentration of agonist that produced half-maximal contraction. After control responses were obtained, tissues were incubated with an appropriate concentration of buffer or antagonist for 1 hour. Responses to serotonin were then repeated in the presence of an antagonist. Concentration responses utilized only one agonist and one antagonist concentration per tissue. In general, successive agonist responses in the presence of buffer treatment were unaltered (average dose ratio was 1.28±0.21).

Apparent antagonist dissociation constants ($K_B$) were determined for each concentration of antagonist according to the following equation:

$$K_B=[B]/(\text{dose ratio-1})$$

where [B] is the concentration of the antagonist and dose ratio is the $ED_{50}$ of the agonist in the presence of the antagonist divided by the control $ED_{50}$. Generally, parallel shifts in the concentration-response curves occurred in the presence of antagonists. The results were expressed as the negative logarithm of the $K_B$ (i.e., -log $K_B$). Calculations were completed using known methods. B. R. Zaborowsky, *J. Pharmacol. Methods*, 4:4165 (1980).

$IP_3$ Formation in 5-$HT_{2B}$ Transformed Cells

Formation and Extraction of $IP_3$: A600K-2-3-MTX cells, grown in suspension, were harvested by centrifugation at 200×g and were resuspended in protein-free cell culture medium. After incubations of the cells (2.5–3×106 cells/tube in 125 μl) at 37° for 10 minutes, 125 μl of the compound of interest, diluted in protein-free medium, were added. All incubations were performed in triplicate. When antagonists were used to inhibit the effect of 5-HT, the cells were incubated with the antagonists for 10 minutes at 37° before the addition of 5-HT. After addition of agonist, the cell suspension was vortexed and incubated for an additional 10 seconds at 37° (the 10 seconds include the time for vortexing). Then 250 μl of ice-cold 10% perchloric acid were added to terminate the reaction. The tubes were incubated for 10 minutes on ice and then centrifuges at 1500×g for 10 minutes. After centrifugation, 400 μl of the supernatant were sampled. The following IP$_3$ extraction procedure was modified from published procedures (E. S. Sharps, et al, A High Performance Liquid Chromatographic Method To Measure $^{32}$P Incorporation Into Phosphorylated Metabolites In Cultured Cells., *Anal. Biochem.* 124:421–424 (1982) and K. A. Wreggett, et al, A Rapic Separation Method For Inositol Phosphates And Their Isomers., *Biochem. J.*, 245:655–660 (1987)). The 400 μl sample was added to a 1.5 ml microfuge tube containing 100 μl of 10 mM EDTA, pH 9.0. This was followed by the addition of 500 μl of 1,1, 2trichlorotrifluroethane/tri-n-octylamine (1:1, v/v). The tubes were vortexed vigorously for 5–7 minutes and then centrifuged at 1500×g for 2 minutes to aid in separation of the three layers. From the top aqueous layer 100 μl were sampled for the determination of IP$_3$ content by the assay described below.

IP$_3$ binding assay: Rat cerebellar membranes were used as the source for the IP$_3$-binding protein in a binding assay modified from published procedures (P. F. Worley, et al, Characterization Of Inositol Triphosphate Receptor binding in brain, *J. Biol. Chem.*, 262:12132–12136 (1987) and D. S. Bredt et al, A Simple, Sensitive, And Specific Radioreceptor Assay For Inositol 1,4,5-Triphosphate In Biological Tissues, *Biochem. Biophys. Res. Commun.*, 159:976–982 (1989)). Membranes were prepared by homogenizing rat cerebella in 30 volumes of homogenization buffer (1 mM EDTA and 1 mM 2-mercaptoethanol in 50 mM Tris.HCl, pH 7.7), using a Tissumizer (Tekmar) at setting 65, for 15 seconds. The homogenate was centrifuges at 39,800×g for 10 minutes at 4°. This procedure was repeated three more times, for a total of four washes. The final pellet was suspended in 30 volumes of IP$_3$ binding buffer (1 nM EDTA and 1 mM 2-mercaptoethanol in 64.3 mM Tris.HCl, pH 9.0) and frozen at −70° until needed.

Binding buffer (350 μl, containing [$^3$H]IP$_3$ and 50 μl of binding protein homogenate were added to 100 μl of the extracted IP$_3$ samples or known IP$_3$ standards that had been subjected to the extraction procedure as described above. The final concentration of [$^3$H]IP$_3$ was 1 nM. The tubes were incubated at 0° for 15 minutes and then filtered through Whatman GF/B filters [pre-wet with water and precooled with 2 ml of ice-cold IP$_3$ wash buffer (1 mM EDTA in 50 mM Tris.HCl, pH 9.0)] by using a Brandel cell harvester. The filters were then rapidly washed two times with 1 ml of ice-cold IP$_3$ wash buffer. The amount of [$^3$H]IP$_3$ trapped on the filters was determined by liquid scintillation counting. The amount of IP$_3$ in the samples was determined by comparison with the standard curve.

When cells expressing the 5-HT$_{2B}$ receptor were preincubated with mianserin, methysergide, rauwolscine, or 1-NP before the addition of 5-HT, the 5-HT curves were shifted to the right and the E$_{max}$ values were decreased, relative to 5-HT alone.

5-HT$_{2A}$ and 5-HT$_{2C}$ Recentor Binding Activity

The ability of a compound to bind to a 5-HT$_{2A}$ or 5-HT$_{2C}$ receptor was measured using standard procedures such as that listed below.

Assay Procedure

Membrane preparation from transformed cell lines. Membranes were prepared using AV12 cells (Syrian hamster fibroblast, ATCC no. CRL 9595) stably transformed with the human-5-HT$_{2A}$, or 5-HT$_{2C}$ receptor (Wainscott et al., Pharmacological Characteristics Of The Newly Cloned Rat 5-Hydroxytryptamine$_{2F}$ Receptor, *Mol. Pharmacol.*, 48:419–426 (1993)). Briefly, cells expressing the receptor of interest were grown in suspension and harvested by centrifugation. The cells were resuspended in a minimal volume of a hypotonic buffer, 50 mM Tris-HCL, pH 7.4, and frozen at 70° C. until needed. On the day the assay, the suspension was thawed and diluted to 35 ml/0.5×10$^2$ cells, original cell number, with 50 mM Tris-HCl, pH 7.4, and centrifuged at 39,800×g, 4° C. The resulting pellet was resuspended by vortexing and incubated at 37° C. for 10 min, then centrifuged at 39,800×g, 4° C. This pellet was resuspended and centrifuged one more time. To achieve a homogenous membrane suspension, the final pellet was resuspended using a Tissumizer (Tekmar, Cincinnati, Ohio) at setting 75 for 10 to 15 sec. in 67 mM Tris-HCl, pH 7.4, for cells expressing the human or rat 5-HT$_{2A}$ receptor or 67 nM Tris-HCl, pH 7.4, containing 13 mM MgCl$_2$ and 0.67 mM EDTA for cells expressing the human 5-HT$_{2C}$ receptors.

5-HT$_{2A,2C}$ [$^{125}$I]DOI binding studies: Human 5-HT$_{2A}$ or 5-HT$_{2C}$ binding studies were performed essentially as described for [$^3$H]5-HT binding to the 5-HT$_{2B}$ receptor with the following exceptions. The assay buffer contained, in final concentration, 10 mM pargyline, 9.75 nM MgCl$_2$, 0.5 mM EDTA, 0.1% sodium ascorbate and 50 nM Tris-HCl, pH 7.4. Incubations were performed at 37° C. for 30 minutes with approximately 40 and 30 mg of protein for the 5-HT$_{2A}$ and 5-HT$_{2C}$ receptors, respectively, then filtered through Whatman GF/C filters which had been presoaked in 0.5% (w/v) polyethylenimine and precooled with 4 ml of ice-cold wash buffer. The filters were then washed rapidly 4 times with 1 ml of ice-cold wash buffer. The amount of [$^{125}$I]DOI trapped on the filters was determined using a gamma counter. Nonspecific binding was determined with 10 mm mianserin for 5-HT$_{2C}$ and 1 mM ketanserin for 5-HT$_{2A}$ receptors. The final concentration of [$^{125}$I]DOI was approximately 0.07 to 0.15 mM for competition experiments.

Statistical analysis: Nonlinear regression analysis for the saturation and competition curves was performed as described previously (Wainscott et al., Pharmacological Characteristics Of The Newly Cloned Rat 5-Hydroxytryptamine$_{2F}$ Receptor, *Mol. Pharmacol.*, 48:419–426 (1993)). One-way analysis of variance was performed on the pK$_1$ values (i.e., log K., molar) followed by the Tukay-Kramer Honestly Significant Difference test (JMP; SAS Institute Inc., Cary, N.C.). IC$_{50}$ values from the competition curves were converted to K$_d$ values using the Cheng-Prusoff (1973) equation. For [$^{125}$I]DOI-labeled receptors, the K$_d$ of [$^{125}$I]DOI for the 5-HT$_{2A}$ or 5 HT$_{2C}$ receptors was determined using a rearrangement of the Cheng-Prusoff equation giving: K$_d$=IC 50-[L], where IC$_{50}$ is the concentration of unlabeled DOI causing 50% inhibition of specific [$^{125}$I]DOI binding and [I]=the free concentration of [$^{125}$I]DOI.

IP$_3$ Formation in 5-HT$_{2A}$ and 5-HT$_{2C}$ Transformed Cells

IP$_3$ formation assay in 5-HT$_{2A}$ and 5-HT$_{2C}$ transformed cells was conducted in the same manner as IP$_3$ formation in 5-HT$_{2B}$ transformed cells with the exception that human AHS1C-3S cells were used for 5-HT$_{2C}$ and human Hu2-3S cells were used for 5-HT$_{2A}$.

The following Experiments are proposed for testing the efficacy of the 5-HT$_2$ antagonists for treating or ameliorating the symptoms of venomous bites or stings.

Experiment #1

The backs of male Wistar rats weighing 250 to 400 g are shaved with an electric clipper 16 to 24 hours before the experiment. On the day of the experiment, rats are anesthetized with Metofane (methoxy flurane) by inhalation. Three concentrations of serotonin, in a volume of 0.05 ml, are injected intradermally with a 26-gauge hypodermic needle. In addition, 0.05 ml of saline is injected intradermally in each animal to indicate the amount of vascular leakage that occurs due to the injection. Sample 1 (6-methyl-1-[(2-chloro-3,4-dimethoxyphenyl)-methyl]-1,2,3,4-tetrahydro-9H-pyrido[3,4-b]indole hydrochloride), Sample 2 (spiro-9,9[2-(3,4-dimethoxy)-1,2,3,4-tetrahydronaphthyl]-5-methyl-1,2,3,9-tetrahydro-8H-pyrido indole), Sample 3 (6-methyl-1-[(2-bromo-3,4-dimethoxyphenyl)-methyl]-1,2,3,4-tetrahydro-9H-pyrido[3,4-b]indole) and Sample 4 (6-iodo-1-[(3,4-dimethoxyphenyl)-methyl]-1,2,3,4-tetrahydro-9H-pyrido[3,4-b]indole hydrochloride) are administered intraperitoneally 15 min. before the intradermal administration of serotonin. Evans blue dye (35 mg/kg) is given intravenously 2 min before intradermal injection of serotonin. To allow for a maximal response, animals are sacrificed by cervical dislocation 30 min after intradermal injection of serotonin. The skin is reflected back and the site (approximately 1–1.5 cm diameter) of each injection is excised. One piece of skin is also taken from an unaffected portion of the back.

Each piece of skin is weighed, placed in 1 ml of 1.0N KOH and incubated at 37° C. for 16 to 20 hr. After addition of 3.3 ml of acetone and 0.7 ml of 1.2N H3PO4, the mixture is vortexed and then centrifuged (400×g, 25 min.). The supernatant is decanted and its optical density read at 620 nm using a Bausch and Lomb Spectronic 710 spectrophotometer. The optical densities of three known concentrations of Evans blue dye are used to construct a standard curve from which the Evans blue dye concentration of the unknown samples is determined. As the total dye in any piece of skin is a combination of intravascular and extravascular dye, we correct for intravascular dye by determining the micrograms of dye per milligram of skin in the unaffected piece of skin and subtracting that amount from each of the other pieces on a per weight basis.

Statistical analysis is performed with an analysis of variance followed by Dunnett's test to compare mean values. Statistical significance is assumed when $P<0.05$.

Results

Serotonin when administered intradermally produces an increase in cutaneous dye extravasation. Samples 1–4 (0.1 and 1.0 mg/kg, i.p.) dose dependently inhibit serotonin-induced increases in cutaneous vascular permeability when administered 15 minutes prior to challenge with intradermal serotonin.

Experiment #2

The backs of male Wistar rats weighing 250 to 400 g are shaved with an electric clipper 16 to 24 hours before the experiment. On the day of the experiment, rats are anesthetized with Metofane (methoxy flurane) by inhalation. Three concentrations of bee venom (natural suspension, Sigma #V 3250), in a volume of 0.05 ml, are injected intradermally with a 26-gauge hypodermic needle. In addition, 0.05 ml of saline is injected intradermally in each animal to indicate the amount of vascular leakage that occurs due to the injection. Evans blue dye (35 mg/kg) is given intravenously 2 min before intradermal injection of bee venom. To allow for a maximal response, animals are sacrificed by cervical dislocation 30 min after intradermal injection of bee venom. The skin is reflected back and the site (approximately 1–1.5 cm diameter) of each injection is excised. One piece of skin is also taken from an unaffected portion of the back.

Each piece of skin is weighed, placed in 1 ml of 1.0N KOH and incubated at 37° C. for 16 to 20 hr. After addition of 3.3 ml of acetone and 0.7 ml of 1.2N $H_3PO_4$, the mixture is vortexed and then centrifuged (400×g, 25 min.). The supernatant is decanted and its optical density read at 620 nm using a Bausch and Lomb Spectronic 710 spectrophotometer. The optical densities of three known concentrations of Evans blue dye are used to construct a standard curve from which the Evans blue dye concentration of the unknown samples is determined. As the total dye in any piece of skin is a combination of intravascular and extravascular dye, we correct for intravascular dye by determining the micrograms of dye per milligram of skin in the unaffected piece of skin and subtracting that amount from each of the other pieces on a per weight basis.

Statistical analysis is performed with an analysis of variance followed by Dunnett's test to compare mean values. Statistical significance is assumed when $P<0.05$.

Results

Bee venom when administered intradermally produces an increase in cutaneous dye extravasation.

Experiment #3

The backs of male Wistar rats weighing 250 to 400 g are shaved with an electric clipper 16 to 24 hours before the experiment. On the day of the experiment, rats are anesthetized with Metofane (methoxy flurane) by inhalation. Three concentrations of bee venom (natural suspension, Sigma #V 3250), in a volume of 0.05 ml, are injected intradermally with a 26-gauge hypodermic needle. In addition, 0.05 ml of saline is injected intradermally in each animal to indicate the amount of vascular leakage that occurs due to the injection. Samples 1–4 are administered intraperitoneally 15 min before the intradermal administration of bee venom. Evans blue dye (35 mg/kg) is given intravenously 2 min before intradermal injection of bee venom. To allow for a maximal response, animals are sacrificed by cervical dislocation 30 min after intradermal injection of bee venom. The skin is reflected back and the site (approximately 1–1.5 cm diameter) of each injection is excised. One piece of skin is also taken from an unaffected portion of the back.

Each piece of skin is weighed, placed in 1 ml of 1.0N KOH and incubated at 37° C. for 16 to 20 hr. After addition of 3.3 ml of acetone and 0.7 ml of 1.2N $H_3PO_4$, the mixture is vortexed and then centrifuged (400×g, 25 min.). The supernatant is decanted and its optical density read at 620 nm using a Bausch and Lomb Spectronic 710 spectrophotometer. The optical densities of three known concentrations of Evans blue dye are used to construct a standard curve from which the Evans blue dye concentration of the unknown samples is determined. As the total dye in any piece of skin is a combination of intravascular and extravascular dye, we correct for intravascular dye by determining the micrograms of dye per milligram of skin in the unaffected piece of skin and subtracting that amount from each of the other pieces on a per weight basis.

Results

Bee venom when administered intradermally produces an increase in cutaneous dye extravasation. Samples 1–4 (0.1 and 1.0 mg/kg, i.p.) dose dependently inhibit bee venom-induced increases in cutaneous vascular permeability when administered 15 minutes prior to challenge with intradermal bee venom.

While it is possible to administer a compound employed in the methods of this invention directly without any formulation, the compounds are usually administered in the form of pharmaceutical compositions comprising a pharmaceutically acceptable excipient and at least one active ingredient (the compound of the present invention). Such compositions contain from about 0.1% by weight to about 90.0% by weight of the present compound. These compositions can be administered by a variety of routes including oral, rectal, topical, transdermal, subcutaneous, intravenous, intramuscular, and intranasal. Many of the compounds employed in the methods of this invention are effective as both injectable, oral and topical compositions. Such compositions are prepared in a manner well known in the pharmaceutical art and comprise at least one active compound. See, e.g., Remington's Pharmaceutical Sciences, (16th ed. 1980).

In making the compositions employed in the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable carriers, excipients and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, tragacanth, gelatin, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compounds of this invention may be delivered transdermally using known transdermal delivery systems and excipients. Most preferably, a compound of this invention is admixed with permeation enhancers including, but not limited to, propylene glycol, polyethylene glycol monolaurate, and azacycloalkan-2-ones, and incorporated into a patch or similar delivery system. Additional excipients including gelling agents, emulsifiers, and buffers may be added to the transdermal formulation as desired.

For topical administration, the compound of this invention ideally can be admixed with any variety of excipients in order to form a viscous liquid or cream-like preparation.

For oral administration, a compound of this invention ideally can be admixed with carriers and diluents and molded into tablets or enclosed in gelatin capsules.

The compositions are preferably formulated in a unit dosage form, each dosage containing from about 0.05 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compounds are generally effective over a wide dosage range. For examples, dosages per day normally fall within the range of about 0.01 to about 30 mg/kg of body weight. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

In order to more fully illustrate the operation of the present invention, the following formulation examples are provided. The examples are illustrative only, and are not intended to limit the scope of the invention. The formulations may employ as active ingredients (compounds) any of the compounds of the present invention.

Formulation Preparation 1

Hard gelatin capsules containing the following ingredients are prepared:

| Ingredient | Quantity (mg/tablet) |
| --- | --- |
| Active Ingredient (s) | 100.0 |
| Starch | 235.0 |
| Magnesium stearate | 5.0 |

The above ingredients are mixed and filled into hard gelatin capsules in 340 mg quantities.

Formulation Preparation 2

A tablet formula is prepared using the ingredients below:

| Ingredient | Quantity (mg/capsule) |
| --- | --- |
| Active Ingredient (s) | 100.0 |
| Cellulose, microcrystalline | 125.0 |
| Colloidal silicon dioxide | 10.0 |
| Stearic acid | 5.0 |

The components are blended and compressed to form tablets, each weighing 240 mg.

Formulation Preparation 3

A dry powder inhaler formulation is prepared containing the following components:

| Ingredient | Weight % |
| --- | --- |
| Active Ingredient (s) | 5 |
| Lactose | 95 |

The active mixture is mixed with the lactose and the mixture is added to a dry powder inhaling appliance.

Formulation Preparation 4

Tablets, each containing 30 mg of active ingredient, are prepared as follows:

| Ingredient | Quantity (mg/tablet) |
| --- | --- |
| Active Ingredients (s) | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50°–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Preparation 5

Capsules, each containing 40 mg of medicament are made as follows:

| Ingredient | Quantity (mg/capsule) |
| --- | --- |
| Active Ingredient (s) | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation Preparation 6

Suppositories, each containing 25 mg of active ingredient are made as follows:

| Ingredient | Amount |
| --- | --- |
| Active Ingredient (s) | 25 mg |
| Saturated fatty acid glycerides to | 2,000 mg |

The active ingredient(s) is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Preparation 7

Suspensions, each containing 50 mg of medicament per 5.0 ml dose are made as follows:

| Ingredient | Amount |
| --- | --- |
| Active Ingredient (s) | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Preparation 8

Capsules, each containing 15 mg of medicament, are made as follows:

| Ingredient | Quantity (mg/capsule) |
| --- | --- |
| Active Ingredient (s) | 15.0 mg |
| Starch | 407.0 mg |
| Magnesium stearate | 3.0 mg |
| Total | 425.0 mg |

The active ingredient(s), cellulose, starch, and magnesium stearate are blended, passed through a No. 20 mesh U.S. sieve, and filled into hard gelatin capsules in 425 mg quantities.

Formulation Preparation 9

An intravenous formulation may be prepared as follows:

| Ingredient | Quantity |
| --- | --- |
| Active Ingredient (s) | 250.0 mg |
| Isotonic saline | 1000 ml |

Formulation Preparation 10

A topical formulation may be prepared as follows:

| Ingredient | Quantity |
| --- | --- |
| Active Ingredient (s) | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation Preparation 11

Sublingual or buccal tablets, each containing 10 mg of active ingredient, may be prepared as follows:

| Ingredient | Quantity Per Tablet |
|---|---|
| Active Ingredient(s) | 10.0 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 mg |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50°–55° C. and the medicament is slowly admixed. The homogenous mixture is poured into forms made of an inert material to produce a drug-containing diffusion matrix having a thickness of about 2–4 mm. This diffusion matrix is then cut to form individual tablets having the appropriate size.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

The type of formulation employed for the administration of the compounds employed in the methods of the present invention may be dictated by the particular compounds employed, the type of pharmacokinetic profile desired from the route of administration and the compound(s), and the state of the patient.

What is claimed is:

1. A method for the treatment or amelioration of the symptoms of a venomous bite or sting in a mammal which comprises administering to the mammal an effective amount of a compound or composition that is a 5-HT receptor antagonist.

2. The method of claim 1 wherein the compound or composition is a 5-$HT_2$ receptor antagonist.

3. The method of claim 2 wherein the 5-$HT_2$ receptor antagonist is a 5-$HT_{2A}$ receptor antagonist.

4. The method of claim 2 wherein the 5-$HT_2$ receptor antagonist is a 5-$HT_{2C}$ receptor antagonist.

5. The method of claim 2 wherein more than one compound or composition is administered.

6. The method of claim 5 wherein each of the 5-$HT_2$ receptor antagonists are receptor antagonists of different receptor subtypes.

7. The method of claim 5 wherein each of the 5-$HT_2$ receptor antagonists are receptor antagonists having an affinity for multiple receptor subtypes.

8. The method of claim 5 wherein the 5-$HT_2$ receptor antagonists are a mixture of receptor antagonists having affinity for single receptor subtypes and receptor antagonists having affinity for multiple receptor subtypes.

9. The method of claim 2 wherein the 5-$HT_2$ receptor antagonist has an affinity for multiple receptor subtypes selected from 5-$HT_{2A}$ and 5-$HT_{2B}$; 5-$HT_{2A}$ and 5-$HT_{2C}$; 5-$HT_{2B}$ and 5-$HT_{2C}$; or 5-$HT_{2A}$, 5-$HT_{2B}$ and 5-$HT_{2C}$.

10. The method of claim 2 wherein the 5-$HT_2$ receptor antagonist is a compound of the formula:

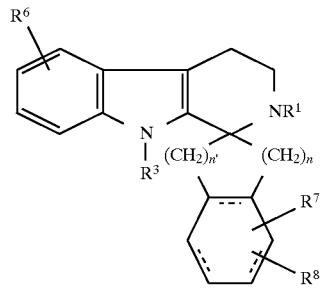

wherein $R^1$ and $R^3$, independently, are hydrogen or $C_1$–$C_3$ alkyl;

$R^6$, $R^7$ and $R^8$, independently, are hydrogen, $C_1$–$C_6$ alkyl, $C_2$–$C_6$ alkenyl, halo, halo($C_1$–$C_6$)alkyl, halo($C_2$–$C_6$) alkenyl, $COR^5$, $C_1$–$C_{10}$ alkanoyl, $CO_2R^{5'}$, $(C_1$–$C_6$alkyl$)_m$amino, $NO_2$, —$SR^5$ or $OR^5$;

n and n', independently are 1, 2, or 3;

m is 1 or 2;

$R^5$ is hydrogen or $C_1$–$C_4$ alkyl;

$R^{5'}$ is $C_1$–$C_4$ alkyl; and

— is optionally a bond; or a pharmaceutically acceptable salt or solvate thereof.

11. The method of claim 2 wherein the 5-$HT_2$ receptor antagonist is a compound of the formula:

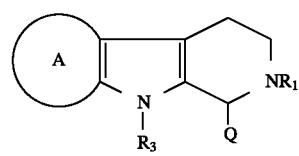

wherein

Q is hydrogen or $(CHR_2)R_4$;

$R_1$, $R_2$ and $R_3$, independently, are hydrogen or $C_1$–$C_3$ alkyl;

$R_4$ is $C_5$–$C_8$ cycloalkyl, phenyl, $C_5$–$C_8$ cycloalkenyl, or a 7- to 12-membered bridged or fused bicyclic carbon ring; or $C_5$–$C_8$ cycloalkyl, phenyl, $C_5$–$C_8$ cycloalkenyl, or a bicyclic ring having up to four substituents independently selected from $C_1$–$C_6$alkyl, $C_2$–$C_6$alkenyl, halo, halo($C_1$–$C_6$)alkyl, halo($C_2$–$C_6$)alkenyl, $COR_5$, $CO_2R_5$, $(C_1$–$C_6$alkyl$)_m$amino, $NO_2$, —$SR_5$, or $OR_5$;

A is

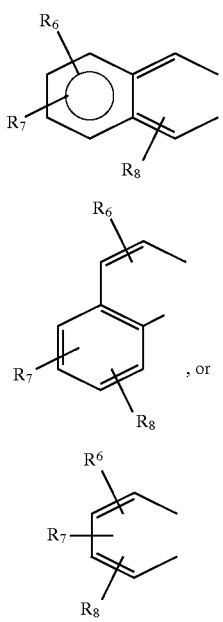

$R_6$ and $R_7$, independently, are hydrogen, $C_1$–$C_6$ alkyl, $C_2$–$C_6$ alkenyl, halo, halo($C_1$–$C_6$)alkyl, halo($C_2$–$C_6$) alkenyl, $COR_5$, $C_1$–$C_{10}$ alkanoyl, $CO_2R_{5'}$, $(C_1$–$C_6$alkyl$)_m$amino, $NO_2$, —$SR_5$, or $OR_5$; or $R_6$ and $R_7$ together with the carbon atoms of group A form a 5- to 8-member carbon ring;

m is 1 or 2;

$R_5$ is hydrogen or $C_1$–$C_4$ alkyl;

$R_{5'}$ is $C_1$–$C_4$ alkyl; and $R_8$ is an $R^6$ group, $C_3$–$C_8$ cycloalkyl, $C_3$–$C_8$ cycloalkyl-($C_1$–$C_3$)alkyl, phenyl, $C_5$–$C_8$ cycloalkenyl, phenyl-($C_1$–$C_3$alkyl), or $C_5$–$C_8$ cycloalkenyl-($C_1$–$C_3$)alkyl; or $C_3$–$C_8$ cycloalkyl, phenyl or $C_5$–$C_8$ cycloalkenyl having up to four substituents independently selected from $C_1$–$C_6$ alkyl, $C_2$–$C_6$ alkenyl, halo, halo($C_1$–$C_6$)alkyl, halo($C_2$–$C_6$)alkenyl, $COR_5$, $CO_2R_{5'}$, $(C_1$–$C_6$alkyl$)_m$amino, $NO_2$, —$SR_5$, or $OR_5$;

or a pharmaceutically acceptable salt or solvate thereof.

* * * * *